(12) United States Patent
Eder et al.

(10) Patent No.: US 6,818,667 B2
(45) Date of Patent: Nov. 16, 2004

(54) EUROTINONES, AND DERIVATIVES THEREOF, PROCESSES FOR PREPARING THEM, AND THEIR USE

(75) Inventors: Claudia Eder, Hofheim (DE); Herbert Kogler, Glashütten (DE); Luigi Toti, Hochheim (DE)

(73) Assignee: Aventis Pharma Deutschland GmbH, Frankfurt am Main (DE)

( * ) Notice: Subject to any disclaimer, the term of this patent is extended or adjusted under 35 U.S.C. 154(b) by 232 days.

(21) Appl. No.: 10/180,003

(22) Filed: Jun. 26, 2002

(65) Prior Publication Data

US 2003/0125375 A1 Jul. 3, 2003

(30) Foreign Application Priority Data

Jun. 27, 2001 (DE) ........................................ 101 30 890

(51) Int. Cl.⁷ ..................... A61K 31/335; C07D 313/06
(52) U.S. Cl. ....................................... 514/450; 549/268
(58) Field of Search ........................... 514/450; 549/268

(56) References Cited

FOREIGN PATENT DOCUMENTS

| DE | 691 32 155 T2 | 12/2000 |
| GB | 2 323 845 | 10/1998 |
| WO | 01/66783 A1 | 9/2001 |

OTHER PUBLICATIONS

Chemical Abstracts, An antifungal antibiotic, eurotin A 54:16644g–i (1960).

*Primary Examiner*—Amelia A. Owens

(74) *Attorney, Agent, or Firm*—F. Aaron Dubberley

(57) ABSTRACT

The present invention relates to novel compounds of the formula I

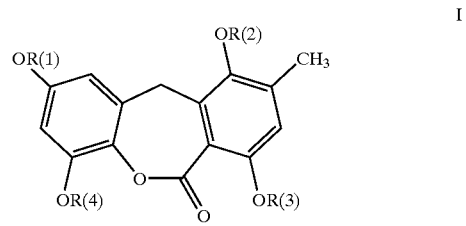

in which R(1), R(2), R(3) and R(4) are, independently of each other, hydrogen or an alkyl radical. The compounds of the formula I are inhibitors of KDR kinase and, due to their antiangiogenic effect, are suitable for preventing and/or treating malignant diseases. The compounds of the formula I can be obtained by fermenting the microorganism *Eurotium echinulatum Delacroix* (DSM 13872) or by chemically derivatizing the compounds which are obtained after fermenting said microorganism. The invention consequently also relates to a process for preparing the compounds of the formula I, to the use of the compounds of the formula I for preparing a pharmaceutical for treating malignant diseases and diseases which can be treated by inhibiting KDR kinase, and also to pharmaceutical preparations which have a content of at least one compound of the formula I.

11 Claims, No Drawings

EUROTINONES, AND DERIVATIVES THEREOF, PROCESSES FOR PREPARING THEM, AND THEIR USE

The present invention relates to novel compounds of the formula I

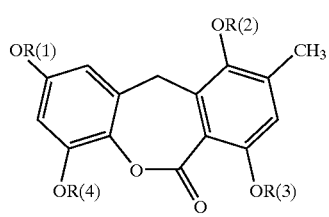

in which R(1), R(2), R(3) and R(4) are, independently of each other, hydrogen or an alkyl radical. The compounds of formula I are inhibitors of the KDR kinase and are suitable, on account of their antiangiogenic effect, for preventing and/or treating malignant diseases. The compounds of the formula I can be obtained by fermenting the microorganism *Eurotium echinulatum Delacroix* (DSM 13872) or by chemically derivatizing the compounds which are obtained after fermenting said microorganism. The invention consequently also relates to a process for preparing the compounds of the formula I, to the use of the compounds of the formula I for producing a pharmaceutical for treating malignant diseases and diseases which can be treated by inhibiting KDR kinase, and to pharmaceutical preparations which comprise a content of at least one compound of the formula I.

Cancer is a disease of humans and animals which often has a fatal outcome and which is caused by the uncontrolled growth of the body's own cells. Cancer is the term for the formation of malignant growths (malignomas) and neoplasms (tumors or carcinomas) or for malignant degeneration and maturation disturbance in white blood cells (leukemia, blood cancer). Cancer cells or tumor cells arise due to the transformation of the body's own cells. malignancy of the cancer cells is expressed in the autonomy of its growth, that is in the ability of the cell to grow in an infiltrating manner, without being inhibited, without being correctly incorporated into the structural plan of the organ, and with the tissue being destroyed. A reliable sign of malignancy is the formation of metastases at a distance from a tumor, following the hematogenic or lymphogenic dispersal of tumor cells. Cancer is one of the most frequent causes of death in humans and there is therefore a great need for methods and means for curing or treating malignant degeneration.

Aside from the operative removal of the tumor, the possibilities of treating malignant tumors include radiological therapy using X-rays, α-rays, β-rays or γ-rays, immunotherapy, and chemotherapy. At present, immunotherapy can only be used to a limited extent. The chemotherapy of tumors is understood as being the administration of cell poisons (cytostatic agents) for treating tumors and tumor cells which have remained following local surgical treatment or irradiation. These substances intervene specifically in particular events in cell division such that tissues which contain a high proportion of dividing cells, such as rapidly growing tumor tissue, react with more sensitivity. Among the compounds used are alkylating compounds, such as cyclophosphamide (The Merck Index, 12th ed. page 463), antimetabolites, such as methotrexate (The Merck Index, 12th ed. page 1025), alkaloids, such as vincristine (The Merck Index, 12th ed. page 1704) and antibiotics, such as daunomycin (The Merck Index, 12th ed. page 479) and adriamycin (The Merck Index, 12th ed. page 581–582). Due to massive side-effects, all these agents suffer from severe disadvantages such that the death of the affected patient is only delayed but not averted. Furthermore, resistances to the cytostatic agents employed can develop in the degenerate (cancer) cells with the result that the medicaments being used no longer have a cytostatic effect but, instead, have a toxic effect as a consequence of the side-effects. In addition, it has been found that the combined or sequential use of cytostatic agents exceeds the activity of a single cytostatic agent (monotherapy) and, as a result, it is possible that the substantial side-effects associated with polychemotherapy are not simply additive. For all these reasons, novel chemotherapeutic agents are urgently required and are therefore being sought world-wide.

The growth of a tumor presupposes that the tumor is being adequately supplied with oxygen, something which is only guaranteed by the tumor being provided with an adequate blood supply (vascularization). Tumors are unable to form new blood vessels (=angiogenesis); instead, they have to induce the surrounding connective tissue to perform this angiogenesis.

The formation of new blood vessels using an already existing vascular system as the starting point is of central importance for embryonic development and organ development. Abnormally increased angiogenesis is observed, inter alia, in rheumatoid arthritis, diabetic retinopathy, and tumor growth (Folkman, 1995, Nat. Med., 1:27–31). Angiogenesis is a complex, multistep process which includes the activation, migration, proliferation and survival of endothelial cells.

In combination with other endothelium-specific signal systems, what are termed the vascular endothelial growth factors (VEGFRs) transmit signals for the migration, proliferation and survival of the endothelial cells. The VEGFR family includes the subtypes VEGFR-1 (Flt-1), VEGFR-2 (KDR) and VEGFR-3 (Flt-4). Whereas VEGFR-1 and VEGFR-2 function as universal regulators of endothelial cells, VEGFR-3 principally controls the growth of the lymphatic vascular system. VEGFRs play a key role in all the stages of the angiogenic process.

Extensive studies carried out in the field of tumor angiogenesis during the last 20 years have described a large number of potential therapeutic targets, e.g. kinases, proteases and integrins. This has led to the discovery of a large number of novel antiangiogenic agents, some of which are already being tested clinically (Jekunen et al., 1997, Cancer Treatment Rev., 23:263–286). Within the context of a chemotherapeutic treatment of tumors, angiogenesis inhibitors could be used both for monotherapy and in a combination therapy together with other cytostatic agents. In addition to this, it is possible to conceive of using them for preventing a tumor from growing once again after a therapy has been completed.

The inhibition or regulation of VEGFR-2 (KDR) is a reaction mechanism which offers a novel approach for treating a large number of solid tumors. Thus, the activation of this tyrosine kinase receptor is crucial for endothelial cell growth and the formation of new blood vessels in association with angiogenesis and consequently has an influence on tumor growth and the formation of metastases. In addition to this, there is new evidence to suggest that the expression of VEGF contributes to survival of tumor cells following radiation therapy or chemotherapy (Lee C. G., Heijn M. et al., 2000, Cancer Research, 60 (19):5565–70). This underlines the importance of KDR inhibitors and the previously known cytostatic agents possibly acting synergistically.

It has been found, surprisingly, that the microorganism *Eurotium echinulatum Delacroix* (DSM 13872) is able to form an active compound which exhibits a pronounced inhibitory effect on KDR kinase and consequently constitutes an effective inhibitor of angiogenesis. The novel compound is termed eurotinone below and is, together with eurotinone derivatives, part of the subjectmatter of the invention.

The present invention therefore relates to compounds of the formula I

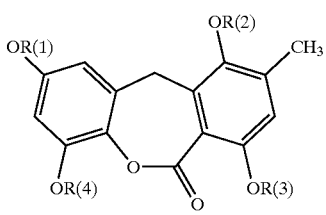

in which

R(1), R(2), R(3) and R(4) are, independently of each other, in each case hydrogen or an alkyl radical, in all the stereochemical forms thereof, and mixtures of these forms in any ratio, and to the physiologically tolerated salts thereof.

An alkyl radical in formula I can, for example, be $(C_1-C_6)$-alkyl, $(C_2-C_6)$-alkenyl, $(C_2-C_6)$-alkynyl, $C_3-C_6$-cycloalkyl, or $(C_1-C_3)$-alkyl-$(C_3-C_6)$-cycloalkyl.

$(C_1-C_6)$-alkyl can be a straight-chain or branched alkyl having from 1 to 6 C atoms, such as methyl, ethyl, i-propyl, tert-butyl and hexyl;

$(C_2-C_6)$-alkenyl can be a straight-chain or branched alkenyl having from 2 to 6 C atoms, such as allyl, crotyl and pentenyl;

$(C_2-C_6)$-alkynyl can be a straight-chain or branched alkynyl having from 2 to 6 C atoms, such as propynyl, butynyl and pentynyl.

Examples of $(C_3-C_6)$-cycloalkyl are cyclopropyl, cyclobutyl, cyclopentyl and cyclohexyl.

The abovementioned alkyl radicals can be substituted by one or more radicals. These can, for example, be halogen, such as chlorine, bromine or fluorine; hydroxyl; alkoxy having 1–4 C atoms, such as methoxy, and/or trifluoromethyl.

R(1)–R(4) in the formula I are in each case, independently of each other, hydrogen or $(C_1-C_6)$-alkyl.

Preference is given, in particular, to compounds of the formula I in which a) R(1)–R(4) are hydrogen (=eurotinone);

b) R(1)–R(3) are hydrogen and R(4) is $(C_1-C_6)$-alkyl, in particular methyl; or c) R(1) and R(2) are hydrogen and R(3) and R(4) are $(C_1-C_6)$-alkyl, in particular methyl; in all the stereochemical forms thereof and mixtures of these forms in any ratio, and also the physiologically tolerated salts thereof.

The invention consequently relates to eurotinone of the formula

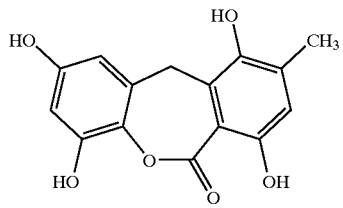

and to the physiologically tolerated salts thereof.

The invention furthermore relates to 2,12-dimethyleurotinone of the formula

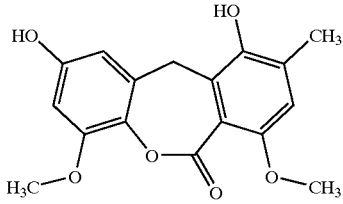

and to 2-methyleurotinone of the formula

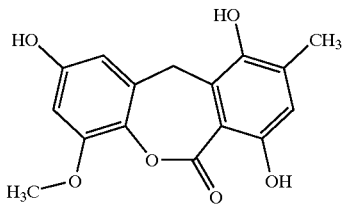

and to the physiologically tolerated salts thereof.

According to the invention, the compounds of formula I can be obtained by fermenting the microorganism *Eurotium echinulatum Delacroix* (DSM 13872), or its variants or mutants, under suitable conditions. The eurotinones are obtained by subsequently isolating the compounds and, where appropriate, converting them into chemical derivatives and into their physiologically tolerated salts.

The invention therefore furthermore relates to a process for preparing a compound of the formula I, which process comprises fermenting the microorganism *Eurotium echinulatum Delacroix* (DSM 13872), or its variants or mutants, under suitable conditions in a culture medium until the eurotinone accumulates in the culture medium or in the microorganism and subsequently isolating the eurotinone from the culture medium or microorganism and, where appropriate, converting it into chemical derivatives and/or physiologically tolerated salts.

A large number of reactions for alkylating phenols have been described in the literature. The alkylation of the phenolic OH groups of the present compounds can therefore be carried out using chemical reactions which are known per se. A derivatization to give the alkylated derivatives of eurotinone can be effected, for example, by reacting the eurotinone with alkyl halides, such as alkyl bromides or alkyl iodides, alkylsulfonic esters, such as mesylates, tosylates or triflates, and also diazoalkanes, such as diazomethylene or trimethylsilyldiazomethane.

The invention is described below in detail.

The eurotinones according to the invention are produced by the fungus *Eurotium echinulatum*, preferably by *Eurotium echinulatum Delacroix* (DSM 13872).

The fungus *Eurotium* possesses a yellow/brown substrate mycelium and little aerial mycelium. In culture it forms the fruiting bodies, i.e. the cleistothecia, which are characteristic for *Eurotium*. The ascospores are flattened, spherical spheres. They possess a typical equatorial crest. The fungus is ubiquitous and prefers dry habitats. The designation *Aspergillus echinulatus* is also still used as a synonym.

An isolate of *Eurotium echinulatum Delacroix* was deposited in the Deutsche Sammlung von Mikroorganismen und Zellkulturen [German collection of microorganisms and cell cultures] GmbH (DSMZ), Mascheroder Weg 1B, 38124 Braunschweig, Germany, in accordance with the rules of the Budapest Treaty, on Nov. 15, 2000, under the following number: DSM 13872.

*Eurotium echinulatum Delacroix* (DSM 13872) produces the eurotinone according to the invention on a solid or liquid culture medium which contains a carbon source and a nitrogen source and the customary inorganic salts.

Instead of the strain *Eurotium echinulatum Delacroix* (DSM 13872), it is also possible to use its mutants and variants which likewise synthesize the eurotinones according to the invention.

These mutants can be generated in a known manner, using physical means, for example irradiation, such as using ultraviolet rays or X-rays, or using chemical mutagenesis, such as ethyl methanesulfonate (EMS), 2-hydroxy-4-methoxy-benzophenone (MOB) or N-methyl-N'-nitro-N-nitrosoguanidine (MNNG), or using recombinant methods.

The fermentation conditions which are described below are valid for *Eurotium echinulatum*, the deposited isolate *Eurotium echinulatum Delacroix* (DSM 13872), and also mutants and variants of these organisms.

The process according to the invention can be employed for fermenting on a laboratory scale (milliliter to liter range) and an industrial scale (cubic meter scale). Unless otherwise indicated, all the percentage values refer to the weight. Unless otherwise indicated, mixing ratios in the case of liquids refer to the volume.

The process according to the invention comprises culturing *Eurotium echinulatum Delacroix* (DSM 13872), its mutants and/or variants, under aerobic conditions in a culture medium containing a carbon source and a nitrogen source, inorganic salts and, where appropriate, trace elements. The strain *Eurotium echinulatum Delacroix* (DSM 13872), forms eurotinone on nutrient solutions containing glucose, starch, rolled oats or glycerol.

Carbon sources which are preferred and suitable for fermentation are assimilable carbohydrates and sugar alcohols, such as glucose, lactose, sucrose or D-mannitol, and also carbohydrate-containing natural products, such as malt extract or yeast extract. Suitable nitrogen-containing nutrients are: amino acids, peptides and proteins and also their breakdown products, such as casein, peptones or tryptones, and, in addition, meat extracts, yeast extracts, ground seeds, for example from corn, wheat, beans, soya or the cotton plant, distillation residues from producing alcohol, meat meals or yeast extract, and also ammonium salts and nitrates, and also, in particular, peptides which are obtained synthetically or biosynthetically. Examples of inorganic salts which can be present in the nutrient solution are chlorides, carbonates, sulfates or phosphates of the alkali metals or alkaline earth metals, iron, zinc, cobalt and manganese.

The eurotinone according to the invention is formed particularly well, for example, in a nutrient solution which contains from about 0.05 to 5%, preferably from 1 to 2%, malt extract, from about 0.05 to 3%, preferably from 0.05 to 1%, yeast extract, from 0.2 to 5%, preferably from 0.5 to 2%, glucose, and from 0.5 to 3%, preferably from 1.5 to 3%, rolled oats. The values in percent are in each case based on the weight of the total nutrient solution.

The microorganism is cultured aerobically, that is, for example, submerged while being shaken or stirred in shaking flasks or fermenters, or on solid medium, where appropriate while introducing air or oxygen. The culture can be carried out in a temperature range of from about 15 to 35° C., preferably at from about 20 to 35° C., in particular at from 25 to 30° C. The pH range should be between 3 and 10, preferably between 6.5 and 7.5. The microorganism is generally cultured under these conditions over a period of 48 to 720 hours, more generally from 72 to 720 hours. Advantageously, the microorganism is cultured in several steps, i.e. one or more precultures are first prepared in a liquid nutrient medium, then inoculated into the actual production medium, i.e. the main culture, for example in a volume ratio of 1:10–1:100. The preculture is obtained, for example, by inoculating the mycelium into a nutrient solution and allowing it to grow for about 20 to 120 hours, generally for about 48 to 72 hours. The mycelium can be obtained, for example, by allowing the strain to grow for about 1 to 40 days, generally for about 15 to 20 days, on a solid or liquid nutrient medium, for example yeast-malt agar, rolled oats agar or potato dextrose agar.

The fungus *Eurotium echinulatum Delacroix* (DSM 13872), can form the compound eurotinone in a surface culture or standing culture on solid nutrient media. Solid nutrient media are prepared by adding, for example, agar or gelatin to aqueous nutrient media. It is also possible, however, to obtain the eurotinone by fermenting the fungus *Eurotium echinulatum Delacroix* (DSM 13872), in the submerged method, i.e. in aqueous suspension. The eurotinone can be present both in the mycelium and in the culture filtrate; the major quantity is normally located in the culture filtrate. If the culture is a liquid culture, the customary methods are first of all employed to separate the mycelium from the culture broth and the eurotinone is then extracted from the cell mass using an organic solvent, which can, if necessary, be miscible with water. The organic solvent phase contains the natural product according to the invention; this phase is concentrated, where appropriate, in vacuo iand purified further as described below.

The culture filtrate is, where appropriate, combined with the concentrate of the mycelium extract and extracted with a suitable organic solvent which is not miscible with water, for example with n-butanol. The organic phase, which is subsequently separated off, is concentrated in vacuo, where appropriate. Preference is given to the culture filtrate being fractionated directly by chromatography, as described below.

The surface culture is expediently first freeze-dried and then extracted with methanol or 2-propanol; however, it is also possible to use other solvents. The resulting extract is then lyophilized.

The further purification of the eurotinone according to the invention is effected by chromatography on suitable materials, e.g. on molecular sieves, on normal phase supports, such as silica gel or aluminum oxide, or on ion exchangers, such as on adsorber resins, and on reversed phases (RPs). This chromatography is used to isolate the eurotinone. The chromatography is carried out using buffered aqueous solutions or mixtures of aqueous and organic solutions.

Mixtures of aqueous or organic solutions are understood as meaning all organic solvents which are miscible with water, preferably methanol, 2-propanol and acetonitrile, at a concentration of from 10 to 80% solvent, preferably of from 15 to 55% solvent, or else all buffered aqueous solutions which are miscible with organic solvents.

Buffered or acidified aqueous solutions are understood as meaning, for example, water, phosphate buffer, ammonium acetate or citrate buffer at a concentration of from 1 mM to 0.5 M, and also formic acid, acetic acid, trifluoroacetic acid or all commercially available acids known to the skilled person, preferably at a concentration of from 0.01 to 3%, in particular 0.1%.

The chromatography is carried out using a gradient which begins with 100% aqueous buffer and ends with 100% solvent, generally 2-propanol or acetonitrile. A linear gradient of from 10 to 60% acetonitrile in buffered aqueous solution is preferably run for purifying the eurotinones according to the invention.

Methods known to the skilled person can be used to convert the eurotinone and derived chemical derivatives of the formula I into the corresponding physiologically tolerated salts.

Physiologically tolerated salts of compounds of the formula I and 11 are understood as meaning both their organic salts and their inorganic salts, as are described in Remington's Pharmaceutical Sciences (17th edition, page 1418 (1985)). Due to their physical and chemical stability and solubility, sodium, potassium, calcium and ammonium salts, inter alia, are preferred for acid groups; salts of hydrochloric acid, sulfuric acid or phosphoric acid, or of carboxylic acids or sulfonic acids, such as acetic acid, citric acid, benzoic acid, maleic acid, fumaric acid, tartaric acid and p-toluenesulfonic acid, are preferred for basic groups.

The present invention encompasses all the stereoisomeric forms of the compounds of the formula I. Centers of asymmetry which are present in the compounds of the formula I can all, independently of each other, have the S configuration or the R configuration. The invention includes all the possible enantiomers and diastereomers, as well as mixtures of two or more stereoisomeric forms, for example mixtures of enantiomers and/or diastereomers, in all ratios. Consequently, enantiomers in enantiomerically pure form, both as levorotatory and as dextrorotatory antipodes, R and S configurations, in the form of racemates and in the form of mixtures of the two enantiomers, in all ratios, are part of the subject-matter of the invention. When a cis/trans isomerism is present, both the cis form and the trans form, and mixtures of these forms, in all ratios, are part of the subject-matter of the invention.

Tests for determining the biological activities of the eurotinones:

The tyrosine kinase receptor KDR is the test target. KDR plays a key role in the growth of endothelium and in angiogenesis and is consequently also involved in the development of tumors. KDR is consequently an important therapeutic target molecule for cancer diseases and other proliferative diseases. In the test, the activity of the KDR kinase is measured on the basis of the phosphorylation of a specific peptide substrate. In addition to their inhibitory activity on said kinases, the eurotinones also inhibit other kinases which are likewise involved in the development of cancer or in the inflammation cascade.

Because of their valuable pharmacological properties, the compounds according to the invention are suitable for use as pharmaceuticals in human and/or veterinary medicine. The compounds according to the invention can be used in association with cancer diseases, in particular as chemotherapeutic agents. Because of their antiangiogenic properties, and the antitumor activity which is associated therewith, they can, in particular, be employed as remedies for malignant degeneration in animals and in humans.

In addition to this, it is possible to conceive of using them for preventing a tumor from growing once again after a therapy has been completed. Within the context of a chemotherapeutic tumor treatment, the eurotinones of the formula I according to the invention can be used both for monotherapy and in a combination therapy together with other cytostatic agents. Because cytostatic agents and angiogenesis inhibitors have different points of attack, the combination therapy can lead to KDR inhibitors and the previously known cytostatic agents having a synergistic effect.

The invention also relates to pharmaceutical preparations which comprise one or more of the eurotinones of the formula I according to the invention and also, where appropriate, a cytostatic agent as well as an additional active compound. Preference is given to using the eurotinones in a mixture with suitable auxiliary substances or carrier materials. All pharmacologically tolerated carrier materials and/or auxiliary substances can be used as carrier materials in humans.

The invention also relates to a process for producing a pharmaceutical according to the invention, which process comprises at least one of the compounds according to the invention being brought, together with a pharmaceutically suitable and physiologically tolerated carrier and, where appropriate, other suitable active compounds, additives or auxiliary substances, into a suitable administration form.

In general, the pharmaceuticals according to the invention are administered orally, locally, rectally, or parenterally. Examples of suitable solid or liquid galenic preparation forms are granules, powders, tablets, sugar-coated tablets, (micro)capsules, suppositories, syrups, emulsions, suspensions, aerosols, drops and injectable solutions in ampoule form, and also preparations having a protracted release of the active compound, in connection with the production of which use is customarily made of carrier substances and additives and/or auxiliary substances, such as disintegrants, binders, coating agents, swelling agents, glidants or lubricants,flavorants, sweeteners and solubilizers. Examples of frequently employed carrier substances or auxiliary substances which may be mentioned are magnesium carbonate, titanium dioxide, lactose, mannitol and other sugars, talc, milk protein, gelatin, starch, vitamins, cellulose and its derivatives, animal or vegetable oils, polyethylene glycols and solvents, such as sterile water, alcohols, glycerol and polyhydric alcohols.

Where appropriate, the dosage units can be microencapsulated for oral administration, in order to delay the release or extend it over a relatively long period, for example by coating or embedding the active compound, in particle form, in suitable polymers, waxes or the like.

Preference is given to producing and administering the pharmaceutical preparations in dosage units, with each unit containing, as the active constituent, a particular dose of one or more compounds of the eurotinones of the formula I according to the invention. In the cases of solid dosage units, such as tablets, capsules and suppositories, this dose can be up to about 500 mg, generally, however, from about 0.1 to 200 mg, and, in the case of injection solutions in ampoule form, be up to about 500 mg, generally, however, from about 0.1 to 100 mg, per day.

The daily dose which is to be administered depends on the bodyweight, age, sex and condition of the patient. However, higher or lower daily doses may possibly also be appropriate. The daily dose can be administered both by means of a once-only administration in the form of a single dosage unit, or else in several smaller dosage units, and by means of the repeated administration of subdivided doses at predetermined intervals.

The invention is clarified in the examples which follow. Percentage values refer to the weight. Unless otherwise indicated, mixing ratios in the case of liquids refer to the volume.

EXAMPLES

Example 1
Preparing a Glycerol Culture of *Eurotium echinulatum Delacroix,* DSM 13872

30 ml of nutrient solution (malt extract 2.0%, yeast extract 0.2%, glucose 1.0%, $(NH_4)_2HPO_4$ 0.05%, pH 6.0) in a sterile 100 ml Erlenmeyer flask were inoculated with the strain *Eurotium echinulatum Delacroix* (DSM 13872), and incubated, at 25° C. and 140 rpm, for 6 days on a rotating shaker. 1.5 ml of this culture were subsequently diluted with 2.5 ml of 80% glycerol and stored at −135° C.

Example 2
Preparing a Preculture of *Eurotium echinulatum Delacroix* (DSM 13872), in an Erlenmeyer Flask 100 ml of nutrient solution (malt extract 2.0%, yeast extract 0.2%, glucose 1.0%, $(NH_4)_2HPO_4$ 0.05%, pH 6.0) in a sterile 300 ml Erlenmeyer flask were inoculated with the strain *Eurotium echinulatum* Delacroix (DSM 13872), and incubated, at 25° C. and 140 rpm, for 7 days on a rotating shaker. Two ml of this preculture were subsequently inoculated for preparing the main cultures.

Example 3
Preparing a Main Culture of *Eurotium echinulatum Delacroix* (DSM 13872), on Solid Medium Plates.

30 sterile 25×25 cm plates were poured using 200 ml of the following nutrient solution: 20 g of malt extract/l, 20 g of rolled oats/l, 2% agar and pH 7.0. These plates were inoculated with 2 ml of a preculture and incubated at 25° C. The maximum production of the eurotinone according to the invention was reached after approx. 360 hours.

Example 4
Preparing a Liquid Main Culture of *Eurotium echinulatum Delacroix* (DSM 13872)

A sterile 300 ml Erlenmeyer flask containing 100 ml of the following nutrient solution: malt extract 2.0%, yeast extract 0.2%, glucose 1.0%, $(NH_4)_2HPO_4$ 0.05%, pH 6, was inoculated with a culture which had been grown on a sloping tube (same nutrient solution but containing 2% agar) or with 2 ml of a preculture (see Example 2) and incubated, at 25° C. and 140 rpm, on a shaker. The maximum production of the eurotinone according to the invention was achieved after approx. 360 hours. A 96 to 144 hour-old submerged culture (inoculation quantity approx. 10%) from the same nutrient solution was sufficient for inoculating fermenters of 10 to 200 l volume. The conditions for these fermenters were:

Temperature 25° C.

Stirring speed: 200 rpm

Aeration 15 l $min^{-1}$.

The formation of foam was suppressed by repeatedly adding ethanolic polyol solution.

The production maximum was reached after approx. 96 to 144 hours.

Example 5
Isolating the Eurotinone from a Fermentation on Solid Medium 150 solid medium plates, which were incubated as described in Example 3, were lyophilized and the lyophilizate was subsequently extracted with methanol (20–30 l). The methanol extract was reduced to 10 l under vacuum and diluted with water to a methanol content of 10%. The diluted extract was subsequently loaded onto a prepared glass column (BPG 100, 4 l internal volume, from Pharmacia Biotech), which was filled with approx. 2 liters of MCl-Gel® CHP-20P Material (adsorber resin from Mitsubishi Chemicals, Japan). The column was eluted with a gradient of 100% water to 100% isopropyl alcohol. The column flowthrough (1 ⅙ min) was collected in fractions (1 l in each case). All the fractions were tested in the KDR assay and the active fractions (fractions 6–14) were pooled. These fractions were reduced under vacuum to about 10 l and this solution was once again diluted with water such that the content of starting solution was 10%. The resulting solution was loaded once again onto a column (see above) which was filled with approx. 1.5 liters of MCl-Gel® CHP-20P material. The column was eluted with a gradient of 100% water to 100% acetonitrile. The column flowthrough (1 ⅙ min) was collected in fractions (1 l in each case) and the fractions (fractions 4–11) which were active in the test were pooled once again. Concentrating these fractions down under vacuum, and subsequently lyophilizing, yielded approx. 16 g of brown powder.

Example 6
Using Chromatography to Purify the Eurotinone

Approx. 2 g of the powder obtained as described in Example 5 were loaded onto a LUNA® 10μ C18 (2) column (size: 50 mm×250 mm, from Phenomenex, Germany) fitted with a LUNA® 10μ C18 (2) precolumn (size: 21.2 mm×60 mm) and chromatographed using a gradient of from 10% to 40% acetonitrile in 0.1% ammonium acetate/water over 40 minutes. The flow rate of the eluent was 125 ml/min and the fraction size was 125 ml. The eurotinone was in fractions 14 and 15. Lyophilizing these fractions yielded approx. 320 mg of enriched eurotinone. A further purification step, by means of HPLC performed on the same RP-18 column as above, was carried out using a gradient of from 20% to 30% in 30 minutes. The eurotinone-containing fractions were combined, desalted and freeze-dried. This resulted in 210 mg of eurotinone (compound 1) (purity >95%). In this case, too, all the fractions from the individual separation steps were investigated in the biotest.

Example 7
Methylating Eurotinone 35 mg (=0.12 mmol) of the eurotinone obtained as described in Example 6 were dissolved in MeOH (5 ml), after which trimethylsilyldiazomethane was added in 6-fold molar excess. The reaction mixture was stirred at room temperature for 30 min and then concentrated down to dryness. The resulting mixture was chromatographically fractionated on a LUNA® 5μ C18 (2) column (size: 10 mm×250 mm). The elution was carried out using a gradient of from 20% to 60% acetonitrile in water, in the added presence of 0.1% ammonium acetate, over 50 min, at a flowrate of 6.5 ml/min. The column flowthrough was collected in fractions (in each case 6.5 ml fractions). Fractions 19–22 contained 7.5 mg of the dimethyl derivative 2,12-dimethyleurotinone (compound 2), while fractions 23–25 contain 6 mg of the monomethyl derivative 2-methyleurotinone (compound 3).

Example 8

Characterizing Eurotinone (compound 1)

The physicochemical and spectroscopic properties of eurotinone can be summarized as follows:

Empirical formula: $C_{15}H_{12}O_6$

Structural formula:

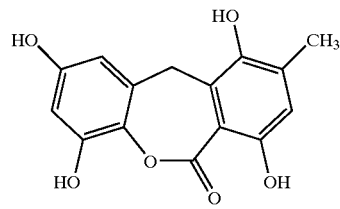

Molecular weight: 288

UV maxima: 200, 262 and 330 nm $^1$H NMR and $^{13}$C NMR: see Table 1

TABLE 1

NMR-chemical shifts of eurotinone, c = 4.5 mg/ml, DMSO-D6 at 300 K

| Position | δ ($^{13}$C) | m ($^{13}$C) | δ ($^1$H) | $^n$J$_{CH}$ |
|---|---|---|---|---|
| 1 | 131.45 | S | — | 6.203, 6.148 |
| 2 | 148.16 | S | — | 6.203 |
| 2-OH | — | — | 9.1 br | — |
| 3 | 101.85 | D | 6.203 | 6.145 |
| 4 | 154.66 | S | — | 6.203, (6.148) |
| 4-OH | — | — | 9.1 br | — |
| 5 | 104.83 | D | 6.148 | 6.203 |
| 6 | 135.13 | s br | — | — |
| 7 | 28.37 | T | 3.79 br | (6.148) |
| 8 | 132.81 | S | — | 2.147 |
| 9 | 142.49 | S | — | 6.576, 2.147 |
| 9-OH | — | — | 8.1 br | — |
| 10 | 130.34 | S | — | (6.578), (2.147) |
| 10-Me | 17.24 | Q | 2.147 | 6.576 |
| 11 | 116.47 | D | 6.576 | 2.147 |
| 12 | 151.53 | S | — | 6.576 |
| 12-OH | — | — | 9.1 br | — |
| 13 | 112.19 | S | — | 6.567, (2.147) |
| 14 | 164.95 | S | — | 6.567 |

Example 9

Characterizing 2,12-dimethyleurotinone (Compound 2)

The physicochemical and spectroscopic properties of 2,12-dimethyleurotinone can be summarized as follows:

Empirical formula: $C_{17}H_{16}O_6$

Structural formula:

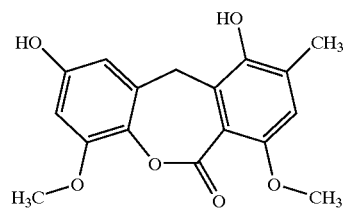

Molecular weight: 316

UV maxima: 200, 262 and 330 nm $^1$H NMR and $^{13}$C NMR: see Table 2

TABLE 2

NMR-chemical shifts of 2,12-dimethyleurotinone, c = 2.5 mg/ml, DMSO-D6 at 300 K

| Position | δ ($^{13}$C) | m ($^{13}$C) | δ ($^1$H) | $^n$J$_{CH}$ | NOE |
|---|---|---|---|---|---|
| 1 | 131.84 | S | — | 6.311, 6.269 | — |
| 2 | 150.16 | S | — | 6.311, (6.269), 3.728 | — |
| 2-OMe | 55.47 | Q | 3.728 | — | 6.311 |
| 3 | 98.57 | D | 6.311 | 9.446, 6.269, 3.728 | 9.446, 3.728 |
| 4 | 154.81 | S | — | 9.446, 6.311, 6.269 | — |
| 4-OH | — | — | 9.446 | — | 6.311, 6.269 |
| 5 | 105.56 | D | 6.269 | 9.446, 6.311 | 9.446, 3.78 |
| 6 | 135.85 | s br | — | — | — |
| 7 | 28.19 | T | 3.78 br | 6.269 | 6.269, 8.385 |
| 8 | 131.35 | S | — | 8.385, (6.765), (2.205) | — |
| 9 | 143.32 | S | — | 8.385, 6.765, 2.205 | — |
| 9-OH | — | — | 8.385 | — | 3.78, 2.205 |
| 10 | 130.91 | S | — | 8.385, 6.765, 2.205 | — |
| 10-Me | 17.37 | Q | 2.205 | 6.765 | 8.385, 6.765 |
| 11 | 112.95 | D | 6.765 | 3.691, 2.205 | 3.691, 2.205 |
| 12 | 151.69 | S | — | 6.765, 3.691 | — |
| 12-OMe | 56.05 | Q | 3.691 | — | 6.765 |
| 13 | 114.67 | S | — | 6.765, (2.205) | — |
| 14 | 162.41 | S | — | 6.765 | — |

Example 10

Characterizing 2-methyleurotinone (Compound 3)

The physicochemical and spectroscopic properties of 2-methyleurotinone can be summarized as follows:

Empirical formula: $C_{16}H_{14}O_6$

Structural formula:

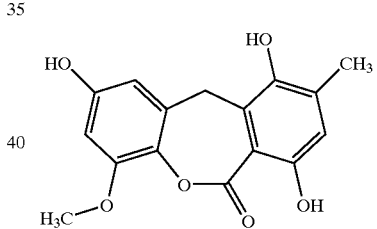

Molecular weight: 302

UV maxima: 200, 262 and 330 nm $^1$H NMR and $^{13}$C NMR: see Table 3

TABLE 3

NMR-chemical shifts of 2-methyleurotinone, c = 2.5 mg/ml, DMSO-D6 at 300 K

| Position | δ ($^{13}$C) | m ($^{13}$C) | δ ($^1$H) | $^n$J$_{CH}$ | NOE |
|---|---|---|---|---|---|
| 1 | 132.16 | s | — | 3.864, 6.249, 6.292 | — |
| 2 | 150.21 | s | — | 3.716, 6.249 | — |
| 2-Me | 55.36 | q | 3.716 | — | 6.249 |
| 3 | 98.41 | d | 6.249 | (3.716), 6.292, 9.207 | 3.716, 9.207 |
| 4 | 155.27 | s | — | 9.207, 6.292, 6.249 | — |
| 4-OH | — | — | 9.207 | — | 6.292, 6.249 |
| 5 | 105.54 | d | 6.292 | 9.207, 6.249, 3.864 | 9.207, 3.864 |
| 6 | 134.64 | s br | — | 3.684 | — |
| 7 | 28.19 | t | 3.864 | 6.292 | 6.292 |
| 8 | 134.62 | s | — | 7.994, 2.144, (9.344) | — |
| 9 | 142.78 | s | — | 7.994, 6.534, 2.144, (3.864) | — |
| 9-OH | — | — | 7.994 | — | 2.144 |

TABLE 3-continued

NMR-chemical shifts of 2-methyleurotinone, c = 2.5 mg/ml, DMSO-D6 at 300 K

| Position | δ ($^{13}$C) | m ($^{13}$C) | δ ($^1$H) | $^n$J$_{CH}$ | NOE |
|---|---|---|---|---|---|
| 10 | 129.16 | s | — | 7.994, (6.534), (3.864), (2.144) | — |
| 10-Me | 17.34 | q | 2.144 | 6.534 | 7.994, 6.534 |
| 11 | 116.59 | d | 6.534 | 9.344, 2.144 | 9.344, 2.144 |
| 12 | 153.30 | s | — | 9.344, 6.534 | — |
| 12-OH | — | — | 9.344 | — | 6.534 |
| 13 | 110.38 | s | — | 9.344, 6.534, (2.144) | — |
| 14 | 166.90 | s | — | 6.534 | — |

Example 11
Investigating the KDR Kinase Activity

The KDR kinase was determined using purified enzyme in 384-well microtiter plates (Coated FlashPlates, NEN Life Science). The enzyme activities were determined by means of phosphorylating a specific peptide substrate. A previously prepared series of dilutions of the eurotinones having concentrations of 100, 50, 25, 12.5, 6.25, 3.125, 1.5625, 0.7813, 0.3906, 0.195, 0.094, 0.047 and 0 µM were pipetted, in the corresponding order, into the experimental assays. The reaction mixture (radioactively labeled ATP, buffer solution at pH 7.4 and enzyme solutions) was then added and the whole was incubated at RT for 1 h.

Description of the KDR assay:
Material and Methods:
Plates: 384-well FlashPlates from NEN life science.
Reader: Wallac MicroBeta Trilux counter
Reagents:
Substrate peptide: PLCγ1
Enzyme: KDR kinase (VEGF receptor)
Kinase Buffer:
50 mM MOPS, pH7.4, 10 mM MgCl$_2$, 2 mM DTT, 2.5 mM EDTA,
10 mM β-glycerophosphate, 1 mM orthovanadate and 1 mM sodium fluoride.
Solution for Coating:
20 µg of peptide substrate/ml in PBS buffer (no Mg$^{++}$, no Ca$^{++}$)
ATP solution: 25µCi of $^{33}$P-γ-ATP/ml and 12.5 µM cold ATP
KDR enzyme solution: 3.5 µg/ml in kinase buffer
Washing solution: PBS (no Mg$^{++}$, no Ca$^{++}$)
384-well FlashPlates were coated, at 40° C. and overnight, with 60 µl (1.2 µg/well) of the peptide substrate and then washed 3×with in each case 80 µl of PBS. The plates which had been coated in this way can be stored for a relatively short time at 4° C. and for a longer period at −20° C.

Reaction: In a final volume of 50 µl, the assay contains 10 µl of diluted eurotinone solution 20 µl of enzyme solution at a concentration of 3.5 µg/ml (70 ng/well) 20 µl of ATP solution (final concentration of 0.5 µCi of hot ATP and 5 µM cold ATP/well)

The reaction mixture was left to stand at room temperature for one hour.

The plates were subsequently washed three times with 75 µl of washing solution in each case and the radioactivity is measured over 30 seconds in a MicroBeta counter (Wallac).

All the samples were tested in duplicate at a final concentration of 1:30. 16 wells were used on each plate for testing the total enzyme activity (=enzyme control). A further 16 wells were coated with 4 µg of casein/well, without substrate, in order to test for nonspecific inhibition.

The activity of the KDR kinase was measured by way of the incorporation of radioactive phosphate from ATP into the substrate, and the inhibitory effect of the eurotinone (IC$_{50}$) was calculated from this incorporation.

The inhibition was calculated as:

[1-(sample CPM-nonspec. CPM)/(enzyme contr. CPM-nonspec. CPM)] × 100 (%).

| IC$_{50}$ values [µM]: | |
|---|---|
| eurotinone (compound 1): | 22 |
| 2,12-dimethyleurotinone (compound 2) | 155 |
| 2-methyleurotinone (compound 3) | 18 |

We claim:
1. A compound of the formula I

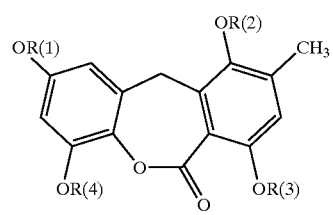

wherein

R(1), R(2), R(3) and R(4) are, independently of each other, hydrogen or an alkyl radical, in all the stereochemical forms thereof, and mixtures of these forms in any ratio, and also the physiologically tolerated salts thereof.

2. The compound as claimed in claim 1, wherein
a) R(1), R(2), R(3) and R(4) are, independently of each other, hydrogen, (C$_1$–C$_6$)-alkyl, (C$_2$–C$_6$)-alkenyl, (C$_2$–C$_6$)-alkynyl, C$_3$–C$_6$-cycloalkyl or (C$_1$–C$_3$)-alkyl-(C$_3$–C$_6$)-cycloalkyl, and
b) the alkyl radicals can, where appropriate, be substituted by one or more radicals.

3. The compound as claimed in claim 1, wherein R(1), R(2), R(3) and R(4) are, independently of each other, hydrogen or (C$_1$–C$_6$)-alkyl.

4. The compound as claimed in claim 1, wherein R(1), R(2), R(3) and R(4) are, independently of each other, hydrogen or methyl.

5. The compound as claimed in claim 1, wherein R(1), R(2), R(3) and R(4) are hydrogen.

6. A compound of the formula

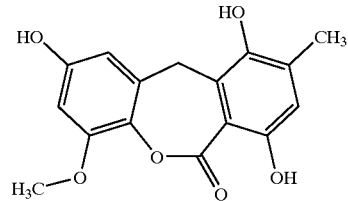

and the physiologically tolerated salts thereof.

7. A compound of the formula

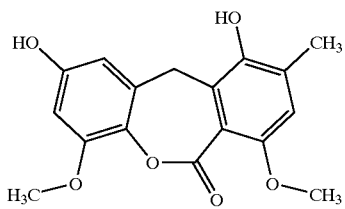

and the physiologically tolerated salts thereof.

8. A pharmaceutical preparation comprising the compound as claimed in any one of claims 1, 6, or 7, or a physiologically tolerated salt thereof.

9. The pharmaceutical preparation as claimed in claim 8, further comprising a cytostatic agent.

10. A method of producing the pharmaceutical preparation as claimed in claim 8, comprising bringing a compound of the formula I, or a physiologically tolerated salt thereof, together with suitable auxiliary substances and/or carrier substances, into a suitable administratable form.

11. A method of producing the pharmaceutical preparation as claimed in claim 9, comprising bringing a compound of the formula I, or a physiologically tolerated salt thereof, together with suitable auxiliary substances and/or carrier substances, into a suitable administratable form.

* * * * *